United States Patent
Mercati

(10) Patent No.: US 9,827,274 B2
(45) Date of Patent: Nov. 28, 2017

(54) ENEMAS

(71) Applicant: ABOCA S.P.A. SOCIETA' AGRICOLA, Sansepolcro (IT)

(72) Inventor: Valentino Mercati, Sansepolcro (IT)

(73) Assignee: ABOCA S.P.A. SOCIETA' AGRICOLA, Sansepolcro (IT)

( * ) Notice: Subject to any disclaimer, the term of this patent is extended or adjusted under 35 U.S.C. 154(b) by 212 days.

(21) Appl. No.: 14/442,533

(22) PCT Filed: Nov. 13, 2013

(86) PCT No.: PCT/IB2013/060094
§ 371 (c)(1),
(2) Date: May 13, 2015

(87) PCT Pub. No.: WO2014/076639
PCT Pub. Date: May 22, 2014

(65) Prior Publication Data
US 2016/0279174 A1 Sep. 29, 2016

(30) Foreign Application Priority Data
Nov. 13, 2012 (IT) .............................. RM2012A0555

(51) Int. Cl.
| A61K 35/644 | (2015.01) |
| A61K 31/045 | (2006.01) |
| A61K 9/00 | (2006.01) |
| A61K 47/10 | (2017.01) |
| A61K 35/63 | (2015.01) |
| A61K 31/047 | (2006.01) |
| A61K 36/185 | (2006.01) |
| A61K 36/53 | (2006.01) |
| A61K 36/752 | (2006.01) |
| A61K 36/886 | (2006.01) |

(52) U.S. Cl.
CPC .......... *A61K 35/644* (2013.01); *A61K 9/0031* (2013.01); *A61K 31/045* (2013.01); *A61K 31/047* (2013.01); *A61K 35/63* (2015.01); *A61K 36/185* (2013.01); *A61K 36/53* (2013.01); *A61K 36/752* (2013.01); *A61K 36/886* (2013.01); *A61K 47/10* (2013.01)

(58) Field of Classification Search
CPC .................................................... A61K 35/644
See application file for complete search history.

(56) References Cited

U.S. PATENT DOCUMENTS

| 8,481,049 B2 | 7/2013 | Ella et al. | |
| 8,754,043 B2 | 6/2014 | Ella et al. | |
| 2006/0099166 A1* | 5/2006 | Vandeputte | .......... A61K 8/8147 424/70.13 |
| 2008/0311216 A1 | 12/2008 | Ella et al. | |
| 2009/0148537 A1* | 6/2009 | Molan | .................. A61K 31/047 424/537 |
| 2009/0324734 A1 | 12/2009 | Dickey | |

FOREIGN PATENT DOCUMENTS

| CN | 1286989 | 3/2001 |
| CN | 101 057 638 | 10/2007 |
| WO | 2006/126212 | 11/2006 |

OTHER PUBLICATIONS

Int'l Search Report for PCT/IB2013/060094, five pages, dated Jan. 14, 2014.
Written Opinion for PCT/IB2013/060094, four pages, dated Jan. 14, 2014.
Anonymous "Glycilax Aäpfchen" *Engelhard Arzneimittel* at www.fachinfo.de/data/fi/jsearch?wirkstoff, two pages (Nov. 2007).
Anonymous "Milk & honey enema" at www.enema-health.com/milk-honey-enema.htm, two pages (Dec. 2009).
Barhate et al. "Processing of honey using polymeric microfiltration and ultrafiltration membranes" *Journal of Food Engineering*, vol. 60, No. 1, pp. 49-54 (Nov. 2003).
Holt "Honey: From old wives' tale to medical product" *Focus on Alternative and Complementary Therapies*, vol. 16, No. 3, pp. 250-251 (Sep. 2011).
Most "Honig—Mel" *Enzyklopädie der Volksmedizin* at www.textlog.de/medizin-honig-mel.html, two pages (1843).
IP Australia, "Notice of Acceptance" for corresponding Australian Application No. 2013346404, three pages, dated Jul. 21, 2016.

* cited by examiner

*Primary Examiner* — Qiuwen Mi
(74) *Attorney, Agent, or Firm* — Nixon & Vanderhye PC

(57) ABSTRACT

The present invention relates to compositions for rectal use comprising honey in a weight percentage up to 95% w/w and glycerine in a weight percentage of between 2-40% w/w for the treatment of constipation in a subject in need thereof. The present invention also relates to a kit of parts comprising such a composition.

20 Claims, No Drawings

ENEMAS

This application is the U.S. national phase of International Application No. PCT/IB2013/060094, filed 13 Nov. 2013, which designated the U.S. and claims priority to Italian Application No. RM2012A000555, filed 13 Nov. 2012; the entire contents of each of which are hereby incorporated by reference.

The present invention relates to compositions for rectal use comprising: honey in a weight percentage up to 95% w/w and glycerine in a weight percentage of between 2-40% w/w for the treatment of constipation in a subject in need thereof. The present invention also relates to a kit of parts comprising such a composition.

STATE OF THE PRIOR ART

The constipation problem affects, sporadically or chronically, a great part of childhood and adult population, and may be the result of insufficient bowel motility or the consequence of various pathologies.

Constipation is caused by overly slow motion of digested material through the colon, leading to excessive water absorption by the intestine.

This event commonly manifests itself in infancy, childhood and adulthood.

The phenomenon is also common during pregnancy and in the postoperative period.

Though many laxative products exist, it is often preferable to intervene in the blandest possible way, avoiding use of oral drugs having too aggressive an effect, or that may interact with other drugs possibly used by the individual suffering from constipation.

Suitably, substances that are not pharmacologically active, i.e. not able to modify metabolic, physiological and biological processes of a living organism according to a direct molecular interaction, can be used. In fact, substances having a "mechanical" action, such as glycerine and the like, not directly activating receptorial or immune pathways or metabolic processes, are preferably used.

In babies, children, pregnant women and in patients' pre- and postoperative stages, the use of rectally administered mechanical stimulants is preferred, i.e. by "enema", the term commonly used when the volume of material introduced into the rectum is, e.g., of about 50, 100, 200 ml and more, also referred to as "paediatric enema" (Fleet type) when the volume is of a few ml and it is commonly prepared also for paediatric or neonatal use.

In this case the substance is introduced rectally, where it directly exerts its mechanical action of evacuation stimulant.

In the most widespread practice enemas or paediatric enemas (Fleet type) are used in which the active ingredient exerting the mechanical effect on the intestine is glycerine or the like.

However, the sole glycerine (or mainly glycerine-based compositions) though able to effectively induce peristaltic movement of intestine, thereby fostering evacuation, produces undesired effects such as abdominal cramps and further irritation and/or dehydration of the mucosa that, in subjects with constipation is already per se irritated and dehydrated. In other terms, glycerine has no beneficial and/or protective effect on intestinal mucosae, with the consequence that use of glycerine as main agent having an evacuating action is often accompanied by low tolerability by the subject suffering from constipation.

It is known in the literature that honey may be used orally as laxative, and that traditional medicine also provided the use of the same in the preparation of enemas, but only at very high dilutions. Moreover, further beneficial activities have been acknowledged to honey, like, e.g., protective activity exerted on mucosae and skin, antimicrobial activity, cicatrizing activity, antitussive activity for the protection of the pharingeal mucosa, antispastic activity in irritable bowel syndrome.

However, honey use did not prove without undesired effects. In fact, e.g., following oral use of honey, where the substance meets natural defenses like saliva and gastric juices before contact with the intestinal mucosa, infant botulism cases were reported, already described in the '70es in the U.S. and with the first case officially recorded in Italy in the '80es. Accordingly, at present paediatricians strongly advise against oral administration of honey to babies and children under 1 year of age.

Also rectal administration of honey to the ends of defecation stimulation did not prove without problems.

In particular, as indicated above, rectally administered honey is always used in a highly diluted form, i.e. in a formulation characterized by low viscosity that causes lower honey tolerability at the level of the intestinal mucosae, in particular the rectal ones. It is known, in fact, that a scarcely viscous composition has quicker interaction kinetics with the mucosae to which it is contacted, with entailed higher aggressiveness of the composition on the mucosae to which it is contacted.

To the above, it should be added that honey diluting for rectal use also entails a decrease of its concentration in the composition and, therefore, a decrease of its effectiveness both in defecatory reflex stimulation and mucosae protection.

Object of the present invention is to overcome the problems present in the state of the art in connection with the use of compositions for rectal use for the treatment of constipation.

SUMMARY OF THE INVENTION

In the present invention it is described a composition for rectal use comprising:
honey in a weight percentage up to 95% w/w
glycerine in a weight percentage of between 2-40% w/w
for the treatment of constipation in a subject in need thereof.

In the present invention a combination of honey and glycerine at the above-indicated concentrations is disclosed which provides a solution to the problems present in the state of the known art, related to the use of substances having an evacuating action and/or solutions comprising them for rectal administration.

In particular, the rectal compositions having an evacuating action comprising honey in highly diluted form as active substance, as highlighted in the preceding section "State of the prior art", are characterized by a low viscosity accompanied by a reduced effectiveness of honey as evacuating agent and, concomitantly, as an agent protecting the intestinal mucosa, in particular the rectal one.

It is known from the literature that both the chemical nature of the active substance on which the composition is based, as well as the interaction kinetics of the same substance with the mucosa, fall among the aspects of a composition which concur to mucosa irritation. In particular, as already highlighted above, interaction kinetics is strongly influenced by composition viscosity, since a low viscosity of the same translates into a quicker interaction kinetics with the mucosae, and consequently into a greater irritating effect of the composition on the mucosae with which it comes into contact.

The Author of the present invention has found that the addition of amounts of glycerine, as diluent, in a weight percentage of between 2-40% w/w to a composition comprising honey in a weight percentage up to 95% w/w significantly increases composition viscosity.

Such a viscosity increase has significant consequences in connection with the beneficial and protective effects of the rectal compositions comprising honey and glycerine for the treatment of constipation as described here. In fact, a higher viscosity causes, as already mentioned, a gentler interaction and a higher mucoadhesion of said compositions with the rectal mucosa, as compared to the same compositions comprising honey but without glycerine. In particular, the increases of viscosity and of mucoadhesion of the compositions object of the present invention advantageously cause a greater lubricating action of the composition, an advantage proving relevant to the beneficial evacuating, yet non-irritating action of the compositions described here.

Therefore, the barrier effect, i.e. the protection effect that the compositions described here exert on the intestinal mucosa, and in particular on the rectal mucosa, is closely related to the above-indicated aspect.

In the present description it is disclosed a composition comprising: honey in a weight percentage up to 95% w/w and glycerine in a weight percentage of between 2-40% w/w for the treatment of constipation, which is particularly advantageous in the treatment of constipation since the mechanical-type evacuation effect (therefore an effect that is not pharmacological, immunological, metabolic) is accompanied by a protective and hydrating action on the intestinal mucosa.

Moreover, the intestinal mucosa being reached anally, without defenses against allergens and bacteria, the possible presence of potentially allergenic pollens, and/or bacteria, in the composition having an evacuating action or even in the substances contained therein, like e.g. honey, which might prove irritating on the intestinal mucosa, has to be considered.

This further problem can be overcome by the use of compositions or honey in accordance with what described here, in which allergenic agents such as pollens have been eliminated (e.g. by honey filtration methods) and/or the bacterial load partially or totally reduced, e.g. by sterilizing the composition or the honey itself (e.g., by gamma ray irradiation).

Therefore, in light of the above, the beneficial and protective effect of the compositions described here on the rectal mucosa can be further improved by allergen elimination and/or bacterial load reduction, subjecting the composition and/or components comprised therein, honey included, to microfiltration and/or ultrafiltration and/or sterilizing processes. Object of the present invention are:

- a composition for rectal use comprising: honey in a weight percentage up to 95% w/w and glycerine in a weight percentage of between 2-40% w/w for the treatment of constipation in a subject in need thereof;
- a package comprising at least two rectal compositions as indicated above;
- a process for the preparation of a composition as described here, depleted of pollens and/or with partial or total reduction of the bacterial load, comprising the step of:
  a. subjecting said composition and/or said honey to one or more microfiltration and/or ultrafiltration steps.
- a kit comprising one or more vessels comprising the composition as described here and one or more further components selected from means for distributing said composition, disposable or reusable devices for the rectal administration of said composition.

DETAILED DESCRIPTION OF THE INVENTION

Therefore, the present invention relates to a composition for rectal use comprising honey in a weight percentage up to 95% w/w and glycerine in a weight percentage of between 2-40% w/w for the treatment of constipation in a subject in need thereof.

The term "constipation" is employed here in its common medical meaning, i.e. to denote substantially an increase of feces stay time in the end part of the intestine. In this condition, an accumulation of dry and hard faecal material is had, due to an excessive reabsorption of liquids, with feces that therefore have scarce volume and are let out infrequently (even less than 3 evacuations/week) and with difficulty and/or pain. In some cases, constipation can also manifest itself with a feeling of incomplete evacuation, in spite of a normal frequency, or with the need of a particular effort by the subject.

As previously highlighted, the innovation at the basis of the composition object of the present invention is the combination between honey and glycerine in the above-indicated percentages, enabling to rectally stimulate evacuation without irritating the intestinal mucosa thanks to the barrier effect that such combination exerts on the mucosae with which it is contacted.

Honey could be present also in minimal concentrations, but compositions wherein the weight percentage is >40%, >50% or even >60%, up to 95% by weight, will be preferred.

Therefore, according to some embodiments, the composition of the invention could comprise the 40%, 50%, 60%, 65%, 70%, 75%, 80%, 85%, 90%, 91%, 92%, 93%, 94% or 95% as ingredient for stimulation of evacuation and therefore in the treatment of constipation.

In one embodiment of the invention, glycerine is present in the compositions described here in a weight percentage of between 10-25% w/w. In particular, glycerine could have a weight percentage of the 10, 11, 12, 13, 14, 15, 16, 17, 18, 19, 20, 21, 22, 23, 24 or 25% w/w.

The glycerine used to the ends of the present invention may be synthetic as well as natural glycerine.

In accordance with a further embodiment, the weight percentage of glycerine in the composition may be of between 14-20% w/w.

In particular, it was observed that when glycerine 18% w/w is added as diluent to a composition comprising honey 75% w/w and water 9% w/w, an increase of viscosity of the starting composition, from a value of about 73 centipoise (cP) to a value of about 570 cP, that is of about 7.8 times, is detected.

The honey, which can be used in combination with glycerine according to the invention described here, could be nectar honey or honeydew honey or a mixture of the two.

In one embodiment, the composition described here comprises nectar honey in a weight percentage of between 60-85% w/w.

In a further embodiment of the invention, the composition comprises honeydew honey in a weight percentage in said composition of between 5-70% w/w. According to a further embodiment of the compositions described here, also the concomitant presence of nectar honey and honeydew honey could be provided, respectively in the above-indicated weight percentages. When a mixture of nectar honey and honeydew honey is present, the honey percentage of the composition will be calculated by adding up both components.

The composition in accordance with the present description could further comprise one or more ingredients such as excipients, plant extracts (e.g., lyophilized, dry, etc.), plant oils, diluting agents, solidifying agents, moisturizing agents, preserving agents, mucilaginous agents, polysaccharide agents.

In one embodiment of the present invention said one or more ingredients are selected from lavender essential oil, aloe extracts, mallow mucilage extracts, calendula extracts, camomile extracts, mallow extracts, althea extracts, propolis, lemon juice, demineralized water and hydromel.

The technician in the field, in the selection of the extracts of the above-indicated officinal plants or of other officinal plants, could refer to state-of-the-art knowledge of plants' officinal properties and will be able to single out with no effort whatsoever which extracts to use according to the present invention.

The amount in weight of each of the further ingredients comprised in the composition according to the present invention, such as those indicated above by way of non-limiting example, could vary, but will be dosed so as to allow observance of honey and glycerine concentrations in the above-defined weight percentages.

According to some embodiments, when extracts are used, aloe extract (leaves) could represent 0.05-1% by weight, e.g. 0.1-0.5% by weight, mallow extract could be a leaf extract and could represent 0.05-5% by weight, e.g. 0.1-2% by weight, calendula extract, as well as camomile (flowers) extract, could each represent 0.05-5% by weight, e.g. 0.1-2% by weight, althea extract and propolis could be used, respectively, at a percentage of between about 0.05-3%, always merely by way of example. In one embodiment, oil of plant origin could be lavender essential oil, and could represent 0.05-2% by weight, e.g. 0.1-1% by weight.

In a further embodiment, lemon juice could represent 0.1-2% by weight.

Such weight percentages are merely indicative and in no way limit the invention to embodiments in which there be used weight percentages different from the ones described above for the additional components (therefore, besides modified honey) present in the compositions.

Merely by way of non-limiting example, the compositions for rectal use for the treatment of constipation in accordance with the present invention may be:

composition 1 (also referred to as "composition AF"): nectar honey 65.7% w/w; honeydew honey 7.3% w/w; Aloe vera, dry extract, 0.1% w/w; lyophilized mallow mucilage extracts 0.1% w/w; lavender essential oil 0.2% w/w; vegetable glycerine 18% w/w; lemon juice 0.5% w/w; demineralized water 8.1% w/w;

composition 2 (also referred to as "composition AE"): nectar honey 73% w/w; Aloe vera, dry extract 0.1% w/w; lyophilized mallow mucilage extracts 0.1% w/w; lavender essential oil 0.2% w/w; vegetable glycerine 15% w/w; natural extracts 3% w/w; lemon juice 0.5% w/w; demineralized water 8.1% w/w;

composition 3 (also referred to as "composition AD"): melt honeydew honey 70% w/w; Aloe vera, dry extract 0.1% w/w; lyophilized mallow mucilage extracts 0.1% w/w; lavender essential oil 0.2% w/w; vegetable glycerine 18% w/w; demineralized water 11.6% w/w;

composition 4 (also referred to as "composition AC"): honeydew honey 70% w/w; Aloe vera, dry extract 0.1% w/w; lyophilized mallow mucilage extracts 0.1% w/w; lavender essential oil 0.2% w/w; vegetable glycerine 18% w/w; hydromel 5% w/w; lemon juice 0.5% w/w; demineralized water 6.1% w/w.

Advantageously, the compositions as described above exert, in association with the evacuating effect at the basis of the treatment of constipation, also at least one effect selected from protective barrier effect, indirect hydrating effect and lubricating and emollient effect on the rectal mucosa. The addition of one or more of the above-described ingredients could further reinforce one or more of the barrier (protective), hydrating, lubricating, emollient effects.

Moreover, the above-indicated additional ingredients could further provide indirect anti-irritating and anti-inflammatory effects.

Any type of honey used in the compositions object of the present invention could, moreover, be depleted of pollens and/or subjected to a partial or total reduction of the bacterial load.

To the ends of the present invention said composition and/or said honey, as well as any ingredient present in the composition itself, could be modified by filtration or by any other means known to the technician in the field eliminating the pollens and/or reducing the bacterial load thereof. Furthermore, the product thus treated could be filtered with a cutoff eliminating also bacteria and their spores, or sterilized so as to carry out a total reduction of the bacterial load, allowing a use of the modified honey obtained also in <1-year-old children.

Filtration, e.g. of honey, could be effectively carried out by techniques known to a person skilled in the art, like, merely by way of example, in accordance with the teachings reported in Subramanian et al "International journal of food properties" 10: 127-143, 2007, in FIG. 1 and pages 128, 138, 139.

Compared to the protocol described by Subramanian et al, to the ends of the present invention the honey could also be not diluted, or less diluted as compared to the 1:1 factor described in the cited document, before carrying out the filtration.

The technician in the field could easily identify suitable filtration membranes adapted for pollen elimination and partial reduction of the bacterial load, or suitable ultrafiltration membranes enabling also a total reduction of the bacterial load as reported in the literature (D'Ascenzi et al (2003) *Rischio da botulismo infantile conseguente a consumo di miele*. Annali della Facoltà di Medicina veterinaria, LVI/20. pp. 63-74) (Lagrange V1991 Ultrafiltration of Honey American Bee Journal, 131, 453). The process could be carried out by standard ultrafiltration or microfiltration techniques, optionally followed by a subsequent process of sterilization of the compositions described here and/or of the sole honey, and more generally of any ingredient comprised in said compositions.

When an ultrafiltration is carried out, a product without pollens and with a total reduction of the bacterial load is obtained, usable also with <1-year-old children. In case, instead, a pollen-eliminating microfiltration is carried out, a product with a reduction of the bacterial load of at least 4 logarithmic units is obtained (Savas 2003 The effects of different technologies on *Alicyclobacillus acidoterrestris* during apple juice production European Food Research and Technology 217, 3, 249-252; and Mukhopadhyay 2011, Removal of *Bacillus anthracis* Sterne spore from commercial unpasteurized liquid egg white, Journal of Food Processing and Preservation, Volume 35, 4, 550-562) usable on >1-year-old children and on adults.

Such a microfiltered product could be further sterilized (as such or in compositions containing it) so as to obtain a total reduction of the bacterial load, with the entailed suitability to the use of the product on <1-year-old children.

In a specific embodiment, the honey could be modified through a filtration process envisaging a first stage of honey heating, an optional dilution thereof and a subsequent step on a filtration system with membranes having a cutoff of 0.45 micron, 0.2 micron, or 0.1 micron.

The membranes could be spiral-wound membranes, ceramics membranes and other membranes known to the technician in the field.

Such process could be carried out directly on honey or on compositions comprising honey and one or more of the further ingredients as indicated in the present description.

Any other process enabling to deplete the composition and/or one or more of the ingredients comprised therein, honey included, of pollens and/or to reduce the bacterial load is suitable for the preparation of the composition according to the invention.

The sterilizing could, e.g., be carried out by treatment with gamma rays, or by thermal treatment (thermal sterilization) or by any other suitable sterilizing technique known to a person skilled in the art.

Merely by way of non-limiting example, the compositions described here could be prepared by using honey microfiltered so as to eliminate pollens and reduce the bacterial load of at least logarithmic units (e.g., at least 4, 5, 6, etc., logarithmic units) and mixing said honey with any further substances, or by microfiltering the entire composition, and the composition thus obtained could be optionally further subjected to sterilizing processes.

A reduction in logarithmic units is a mathematical term for logarithmically defining the reduction in the number of living bacteria. It denotes the relative number of living bacteria eliminated from a sample following a treatment.

A reduction of the bacterial load equal to one logarithmic unit means that the number of bacteria in the sample of interest is 10 times lower after the treatment, a reduction of 2 units indicates a reduction equal to 100 times, of 3 to 1000 times, etc. Alternatively, the composition could be prepared by ultrafiltering the honey so as to eliminate pollens and totally reduce the bacterial load, and mixing said honey with possible further substances, optionally sterilized, or by ultrafiltering the entire composition.

The composition thus obtained could be optionally further subjected to sterilizing processes.

The present invention also relates to a process for the preparation of a composition according to claim 8, comprising the step of:

a. subjecting said composition and/or one or more of the ingredients comprised therein, honey included, to one or more microfiltration and/or ultrafiltration steps. Said microfiltration could be carried out on membranes having a cutoff of about 0.45 micron, 0.2 micron, or 0.1 micron.

Before step a. said honey could be suitably diluted with water or physiological solution, or with further suitable ingredients, and/or heated to a temperature of between about 30 and 70° C.

Said ultrafiltration could be carried out on membranes having a cutoff of about 10,000, 20,000, 50,000, or 100,000 Daltons.

Moreover, the above-described process could also comprise a step of:

b. subjecting the composition and/or one or more of the ingredients comprised therein, honey included, to a sterilizing procedure.

The sterilizing could, e.g., be carried out by treatment with gamma rays, or by thermal treatment (thermal sterilization) or by any other suitable sterilizing technique known to a person skilled in the art.

In one embodiment, the sterilizing is carried out by gamma ray irradiation.

The composition for rectal use as described here could be used to make enemas or paediatric enemas (Fleet type), that in one embodiment can be disposable, by introduction of the composition as prepared in suitable disposable devices apt to the inletting thereof into the rectum.

Such devices will be made so as to have a hollow and elongate portion, substantially cylindrical, to be introduced into the anus, and an external container connected to said portion enabling the propulsion of the composition contained therein into the patient's rectum.

The hollow and elongate portion and the external reservoir could be of different sizes, depending on whether a use for adults, children or babies be envisaged.

Moreover, in the case of a veterinary use, said components of the disposable device will be proportional to the patients for which are intended.

The reservoir for paediatric enemas (Fleet type) will normally contain an amount of composition of between about 1 and 20 ml, e.g. between 5 and 15 ml, the reservoir for enemas could contain volumes of between 20 ml and 500 ml and, when required, volumes even greater. The enemas or the paediatric enemas as described here are therefore suitable to a paediatric use (babies, children) or could be also suitable to a use in adult patients.

Merely by way of example, if the paediatric enema is intended to be used by adults, it could contain 10 g of the composition according to the present invention. Alternatively, if the paediatric enema is intended for paediatric use it could contain 5 g of the composition object of the present description.

The enemas or paediatric enemas of the invention could also be delivered in packages comprising two or more disposable pieces as described here.

The invention also relates to a kit of parts comprising one or more vessels comprising the composition of the invention and one or more further components selected from means for distributing said composition, disposable or reusable means for the rectal administration of said composition.

The composition could therefore be present in the kit in one or more vessels, such as flasks or bottles, and the kit could comprise graduated means like syringes or pipetted for distributing the composition in devices for the administration of the composition in the form of paediatric enemas (Fleet type) or enemas.

Such devices could be disposable or reusable and could be the classic enemas known in the state of the art or devices as the above-described ones.

In a specific embodiment, the device for the administration of the composition, or at least the substantially cylindrical part for introduction into the anus could be of material enabling the sterilizing thereof by the use of sterilizing products or procedures for household use. Such materials could be, e.g., plastics or natural rubber or other materials commonly used in paediatric and non-paediatric medicine.

Alternatively, the devices for the administration of the composition or their parts could be sterile and individually packaged.

Therefore, the invention also relates to a process for the preparation of disposable enemas or paediatric enemas (Fleet type) comprising the composition according to the invention aliquoted in suitable containers.

The following examples are aimed at illustrating some embodiments of the invention and experimental mucoadhesivity data on the oral mucosa; of course, they are not intended as limiting the invention.

EXAMPLES

Example 1

Viscosity Measurements

The study of honey-glycerine interactions was carried out by measuring the viscosity variation of the compositions below:

composition AF (also referred to as "composition 1" in the detailed description): nectar honey 65.7% w/w; honeydew honey 7.3% w/w; Aloe vera, dry extract 0.1% w/w; lyophilized mallow mucilage extracts 0.1% w/w; lavender essential oil 0.2% w/w; vegetable glycerine 18% w/w; lemon juice 0.5% w/w; demineralized water 8.1% w/w;

composition AE (also referred to as "composition 2" in the detailed description): nectar honey 73% w/w; Aloe vera, dry extract 0.1% w/w; lyophilized mallow mucilage extracts 0.1% w/w; lavender essential oil 0.2% w/w; vegetable glycerine 15% w/w; natural extracts 3% w/w; lemon juice 0.5% w/w; demineralized water 8.1% w/w;

composition AD (also referred to as composition 3 in the detailed description): melt honeydew honey 70% w/w; Aloe vera, dry extract 0.1% w/w; lyophilized mallow mucilage extracts 0.1% w/w; lavender essential oil 0.2% w/w; vegetable glycerine 18% w/w; demineralized water 11.6% w/w;

composition AC (also referred to as "composition 4" in the detailed description): honeydew honey 70% w/w; Aloe vera, dry extract 0.1% w/w; lyophilized mallow mucilage extracts 0.1% w/w; lavender essential oil 0.2% w/w; vegetable glycerine 18% w/w; hydromel 5% w/w; lemon juice 0.5% w/w; demineralized water 6.1% w/w.

Viscosity measurements were carried out by using a Brookfield viscometer as known to the technician in the field. In Table 1 below the results of measurements carried out are reported, indicating how glycerine introduction leads to a significant increase of compositions viscosity.

TABLE 1

| Composition | Viscosity w/o glycerine | Viscosity w glycerine |
| --- | --- | --- |
| AF | 72 | 573 |
| AE | 66 | 659 |
| AD | 79 | 640 |
| AC | 81 | 950 |

In the above-described experiments, it was observed that by decreasing water content in favor of glycerine the viscosity increases, thereby indicating that a relationship exists between viscosity increase and glycerine presence. Said data are summarized in Table 2 below.

TABLE 2

| Nectar honey | honeydew honey | water | glycerine | viscosity |
| --- | --- | --- | --- | --- |
| 67 | 7 | 27 | 0 | 70 |
| 67 | 7 | 18 | 9 | 137 |
| 67 | 7 | 13.5 | 13.5 | 280 |
| 67 | 7 | 9 | 18 | 570 |

This conclusion is further corroborated in the battery of experiments reported in Table 3 below, where it is highlighted that by keeping water amount stationary and increasing glycerine amount, the viscosity of the compositions under examination increases.

TABLE 3

| Nectar honey | honeydew honey | water | glycerine | viscosity |
| --- | --- | --- | --- | --- |
| 67 | 7 | 10 | 0 | 110 |
| 67 | 7 | 10 | 9 | 200 |
| 67 | 7 | 10 | 13.5 | 315 |
| 67 | 7 | 10 | 18 | 570 |

Example 2

Process for the Preparation of Modified Honey or of the Compositions According to the Invention To nectar honey, honeydew honey or a mixture thereof, a percentage of water was added in accordance with what described here, and the honey thus diluted was subjected to heating at a temperature of between 40 and 70° C.

Then, one or more steps were carried out on a filtration system with membranes having a cutoff of between 0.45 micron, 0.2 micron, or 0.1 micron and the permeate, which is the product to be used in the formulation, was recovered. At this point, the product thus obtained can be mixed with one or more of the further ingredients, included glycerine at the weight percentages as defined in the present description. Optionally, a sterilizing procedure by gamma ray irradiation or thermal (UHT) treatment may be carried out in case the bacterial (that is, microbial and sporulent) load that may be naturally present in the honey is to be totally reduced.

Example 3

Process for the Preparation of Modified Honey or of the Compositions According to the Invention Nectar honey, honeydew honey or a mixture thereof and, if desired, one or more of the above-described further ingredients, glycerine included, were mixed and the mixture thus obtained was subjected to one or more steps on an ultrafiltration system with a 10,000, 20,000, 50,000, or 100,000 Dalton membrane.

The permeate, which is the product to be used in the formulation, was recovered.

The product exhibited a total reduction of the bacterial load. Optionally, when the further ingredients, glycerine included, for the preparation of the composition are not added before ultrafiltration, a sterilizing procedure can be carried out by gamma ray irradiation or thermal (UHT) treatment in case the bacterial (that is, microbial and sporulent) load that can naturally be present in the honey is to be totally reduced.

Example 4

Mucoadhesion Assays Used

One of the substantial differences between skin structure and mucosae structure is represented by the absence, in the mucosae, of a selective barrier like the stratum corneum. Therefore, a contact of oral mucosae with noxious or irritating substances present in the environment (pollutants, pathogenic microorganisms, etc.) can cause a high penetration of said substances both inside the mucosae and in the related airways (bronchi, lung etc.), causing inflammatory and/or allergic pathologies.

In the present example, the mucoadhesive ability of the compositions comprising honey and glycerine as described here on oral mucosa in vitro was assessed.

In the model, mucoadhesivity was determined by assessment of the percentage of lectin/glycoprotein bond inhibition. In this model, e.g., buccal or vaginal mucosal cells can be used. The cells were treated with biotinylated lectin (Con-A), having a high affinity for the glucoside and mannoside residues present in the glycoproteins of the membrane. The sites of the glycoproteins of the mucosal membranes are thus occupied with the biotinylated lectin. The presence of Biotin (Vitamin H) in the lectin is indispensable for the next stage. The cells already treated with biotinylated lectin are charged with streptavidin peroxidase, making it possible to form the protein/glucose/lectin/biotin/streptavidin peroxidase complex due to the high affinity between biotin and streptavidin. At this point, the cells were washed and the protein-protein/glucose/lectin/biotin/streptavidin peroxidase complex were quantified, thanks to the presence of the peroxidase, by means of a reaction of oxidation of the ortho-phenylenediamine.

The protein/glucose/lectin/biotin/streptavidin peroxidase complex catalyzes the polymerization reaction:

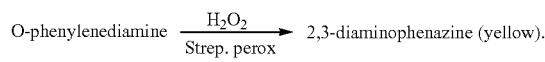

O-phenylenediamine $\xrightarrow[\text{Strep. perox}]{H_2O_2}$ 2,3-diaminophenazine (yellow).

The intensity of the yellow/orange coloration of the solution (measured using a spectrophotometer with =450 nm) is proportional to the quantity of glycoprotein-lectin bonds and therefore to the quantity of available sites (glycoproteins) for mucoadhesion. The absorbency value thus determined constitutes the "control".

In the mucoadhesion assay reported below, the mucosal cells were treated with the product under examination at 30° C. for about 15 minutes before the treatment with lectin. In the presence of mucoadhesive products, these will inhibit the lectin bond, decreasing proportionally to their mucoadhesive ability the signal strength in the sample with respect to the control as above-described.

The percentage of mucoadhesion of the product (% MA) could be determined as

% MA=(1−abs sample/abs control)×100

Example 5

Assessment of Mucoadhesive Ability of a Composition Comprising 74% by Weight of Honey and 18% by Weight of Glycerine The oral cavity of 8-10 male and female donors (age: 20-35 years), without food for at least 60 minutes, was gently scraped with a wooden spatula and the cells immersed in 0.05 M TBS (Tris Buffer Saline) pH 7,6. After count with 0.5% Tripan blue, the cells were diluted with 0.9% NaCl until obtaining a final concentration of 480,000 cells for each sample to be used in the assaying. Cells were kept at a temperature of 4° C. Cellular suspensions were then centrifuged at 2000 rpm for 5 minutes and incubated with 5 ml of a composition comprising 74% by weight of honey and 18% by weight of glycerine. For the control, the cellular suspensions were instead incubated with 5 ml of 0.9% NaCl. Incubation was carried on for 15 minutes at the temperature of 30° C., with gentle stirring. After 3 washings with TBS, the buccal cells were incubated with 5 ml of 10 mg L-1 of Con-A at 30° C. for 30 minutes, washed 3 times with TBS and then incubated at 30° C. for 60 minutes with 5 ml of 5 mg L-1 of streptavidin peroxidase. After 3 washings with TBS, 240,000 cells per sample were added to 2.5 ml of o-phenylendiamine (o-pd) in 0.05 M phosphate citrate and $H_2O_2$ and the reaction was stopped after 5 minutes with 1 M $H_2SO_4$.

Then, absorbency values for the individual determinations were read by spectrophotometer. Since the composition has a coloration that might interfere with the exact determination of the absorbency value recorded at the end of the protocol, for sample reading a (0.9%) NaCl solution (for the control) or the solution of the product suitably diluted with the 0.9% NaCl solution were used as blank. The individual samples were assayed 3 times and the results reported represent the averages±SEM of all assays performed.

| Samples | % mucoadhesion |
| --- | --- |
| A | 97.6 |
| B | 89.2 |
| C | 93.4 |
| Average ± SD | 93.4 ± 4.2 |

The results obtained demonstrate that the assayed composition possesses a high mucoadhesive ability with respect to oral cavity mucosae. In light of the results obtained, it is possible to confirm that the composition, demonstrating to possess high, resistant mucoadhesivity, can play an interesting protective role on cells of the intestinal mucosa, including those of the rectal mucosa.

REFERENCES

D'Ascenzi C et al. Rischio da botulismo infantile conseguente a consumo di miele. Annali della Facoltà di Medicina veterinaria, 2003 LVI/20. pp. 63-74.

Mukhopadhyay 2011, "Removal of Bacillus anthracis sterne spore from commercial unpasteurized liquid egg white" Journal of Food Processing and Preservation Volume 35, 4, 550-562, Savas 2003 "The effects of different technologies on Alicyclobacillus acidoterrestris* during apple juice production" European Food Research and Technology 217, 3, 249-252;

Subramanian et al 2007: "International journal of food properties" 10: 127-143 "Processing honey: a review".

The invention claimed is:

1. A composition for rectal use comprising:

honey in a weight percentage greater than 50% w/w and glycerine in a weight percentage of between 10-25% w/w.

2. The composition according to claim 1, wherein said honey is nectar honey or honeydew honey or a mixture thereof.

3. The composition according to claim 2, wherein said nectar honey is in a weight percentage of between 60-85% w/w and said honeydew honey is in a weight percentage of between 5-70% w/w.

4. The composition according to claim 1, wherein said honey is in a weight percentage greater than 60% w/w.

5. The composition according to claim 1, wherein said glycerine is in a weight percentage of between 14-20% w/w.

6. The composition according to claim 1, further comprising one or more ingredients selected from the group consisting of excipients, plant extracts, plant oils, diluting agents, solidifying agents, moisturizing agents, preserving agents, mucilaginous agents, and polysaccharide agents.

7. The composition according to claim 6, wherein said one or more ingredients are selected from the group consisting of lavender essential oil, aloe extracts, mallow mucilage extracts, calendula extracts, camomile extracts, mallow extracts, althea extracts, propolis, lemon juice, demineralized water, and hydromel.

8. The composition according to claim 1, wherein said composition is depleted of pollens and/or is subjected to a partial or total reduction of bacterial load.

9. Composition according to claim 1, in the form of an enema or paediatric enema of Fleet type.

10. The composition according to claim 9, wherein said enema or paediatric enema is in a disposable formulation.

11. A process for preparation of the composition according to claim 8, comprising the step of:
   a. subjecting said composition and/or said honey to one or more microfiltration and/or ultrafiltration steps.

12. The process according to claim 11, wherein said microfiltration is carried out at a cutoff of about 0.45 μm, 0.2 μm, or 0.1 μm.

13. The process according to claim 11, wherein said ultrafiltration is carried out at a cutoff of about 10,000, 20,000, 50,000, or 100,000 Daltons.

14. The process according to claim 11, further comprising the step of:
   b. subjecting said composition and/or said honey to a sterilizing procedure.

15. The process according to claim 14, wherein said sterilizing procedure is carried out by gamma ray irradiation.

16. A package comprising at least two rectal compositions, wherein each composition comprises:
   honey in a weight percentage greater than 50% w/w and glycerine in a weight percentage of between 10-25% w/w.

17. A kit of parts for use in treatment of constipation in a subject in need thereof, comprising one or more vessels comprising the composition according to claim 1, and one or more further components selected from the group consisting of means for distributing said composition, and disposable or reusable devices for rectal administration of said composition.

18. A kit of parts according to claim 17, wherein said disposable or reusable devices are enemas or paediatric enemas of Fleet type.

19. A method for use of the composition according to claim 1, comprising the step of:
   a. administering rectally said composition to treat constipation in a subject in need thereof.

20. The composition according to claim 1, further comprising additional formulating agents suitable for a pharmaceutical composition.

* * * * *